United States Patent [19]

Kaplan et al.

[11] Patent Number: 5,622,861

[45] Date of Patent: Apr. 22, 1997

[54] RECOMBINANT DNA ENCODING HEPATITIS A VIRUS RECEPTOR

[75] Inventors: Gerardo Kaplan, Rockville, Md.; Stephen M. Feinstone, Washington, D.C.

[73] Assignee: The United States of America as represented by the Department of Health and Human Services, Washington, D.C.

[21] Appl. No.: 287,001

[22] Filed: Aug. 5, 1994

[51] Int. Cl.$^6$ .............................. C12N 5/10; C12N 15/12
[52] U.S. Cl. ................. 435/252.3; 435/69.1; 435/320.1; 530/750; 536/73.5
[58] Field of Search .............................. 435/69.1, 252.3, 435/350.1; 536/23.5

[56] References Cited

PUBLICATIONS

Collier and Wolstenholme *FEMS Microbiol. Letters* 116:183–188, 1994.
Carré and Schiff *Current Opinion in Gasterenterol.* 9:349–354, 1993.
Pensiero et al. *J. Virol.* 66(7):4028–2039, Jul. 1992.
Anderson et al. Abstract P5–1, *Third Internat'l Symposium on Positive Strand RNA Viruses* Clearwater, FL Sep. 19–14, 1992.
Stapleton et al. *J. Infect. Dis.* 164:1098–1103, 1991.
Zajac et al. *J. Gen. Virol.* 72:1667–1675, 1992.
Stapleton and Frederick *Clinical Res.* 37(4):911A, Sep. 1989.
Totsuka et al. Abstract "Preparation of Monoclonal Antireceptor Antibodies with Inhibitory Effect on Hepatitis A Virus Infection", *Japanese Society of Virol.*, 1988.
Seganti et al. *Med. Microbiol. Immunol.* 176:21–26, 1987.

*Primary Examiner*—John Ulm
*Attorney, Agent, or Firm*—Needle & Rosenberg, P.C.

[57] ABSTRACT

Provided is the discovery and isolation of a cellular receptor for hepatitis A virus. Also provided is an isolated nucleic acid molecule comprising a nucleic acid encoding a polypeptide having the biological activity of a hepatitis A virus receptor. Also provided are vectors comprising the isolated nucleic acids encoding a hepatitis A virus receptor in host suitable for expression of the nucleic acids encoding the hepatitis receptor, fragments of the hepatitis A virus receptor, or homologs of the hepatitis A virus receptor. Further provided is a nonhuman transgenic animal which expresses a hepatitis A virus receptor, but does not express an endogenous, active hepatitis A virus receptor. Also provided is a method for screening drugs or vaccines utilizing the transgenic animal expressing a hepatitis A virus receptor. Also provided are methods for use of the purified hepatitis A virus receptor, such as separating hepatitis A virus from blood or other samples, detecting the presence of hepatitis A virus in a sample, determining the anti-hepatitis A virus binding of a compound, preventing hepatitis A virus infection in a subject, or treating a subject infected with hepatitis A virus. Also provided are nucleic acids which selectively hybridize with the nucleic encoding the hepatitis A virus receptor of the present invention.

8 Claims, 1 Drawing Sheet

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2093 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: CDS
        ( B ) LOCATION: 196..1551

( x i ) SEQUENCE DESCRIPTION: SEQ ID NO:1:

```
GCGCGTAGGT  TTAGTTTTTG  AAGTTCTTCT  GTGGACCCTT  TTTGCTTATT  ATATCAATCC        60

TTGGTGGGAG  ACAGAGGAAA  CATTTTTAGT  GCTATTTTAC  AACTGAGGAA  ATAGAGGTTT       120

GAAGAGAACT  CAGGAAGGCT  CAGGGTTATC  CAGCATTGTG  AGTGACAGAG  CTTGGATCTG       180

AACGCTGATC  CCATA ATG CAT CTT CAA GTG GTC ATC TTA AGC CTC ATC CTA            231
                 Met His Leu Gln Val Val Ile Leu Ser Leu Ile Leu
                  1               5                   10

CAT CTG GCA GAT TCT GTA GCC GAT TCT GTA AAT GTT GAT GGA GTG GCA              279
His Leu Ala Asp Ser Val Ala Asp Ser Val Asn Val Asp Gly Val Ala
         15                  20                  25

GGT CTA TCT ATC ACA CTG CCC TGC CGC TAC AAC GGA GCT ATC ACA TCC              327
Gly Leu Ser Ile Thr Leu Pro Cys Arg Tyr Asn Gly Ala Ile Thr Ser
     30                  35                  40

ATG TGC TGG AAT AGA GGC ACA TGT TCT GTT TTC TCA TGC CCA GAT GGC              375
Met Cys Trp Asn Arg Gly Thr Cys Ser Val Phe Ser Cys Pro Asp Gly
 45                  50                  55                  60

ATT GTC TGG ACC AAT GGA ACC CAC GTC ACC TAT CGG AAG GAG ACA CGC              423
Ile Val Trp Thr Asn Gly Thr His Val Thr Tyr Arg Lys Glu Thr Arg
                 65                  70                  75

TAT AAG CTA TTG GGG AAC CTT TCA CGC AGG GAT GTC TCT TTG ACT ATA              471
Tyr Lys Leu Leu Gly Asn Leu Ser Arg Arg Asp Val Ser Leu Thr Ile
             80                  85                  90

GCA AAT ACA GCT GTG TCT GAC AGT GGC ATA TAT TGT TGC CGT GTT AAG              519
Ala Asn Thr Ala Val Ser Asp Ser Gly Ile Tyr Cys Cys Arg Val Lys
         95                  100                 105

CAC AGT GGG TGG TTC AAT GAC ATG AAA ATC ACC ATA TCA CTG AAG ATT              567
His Ser Gly Trp Phe Asn Asp Met Lys Ile Thr Ile Ser Leu Lys Ile
     110                 115                 120

GGG CCA CCC AGA GTC ACT ACT CCA ATT GTC AGA ACT GTT CGA ACA AGC              615
Gly Pro Pro Arg Val Thr Thr Pro Ile Val Arg Thr Val Arg Thr Ser
125                 130                 135                 140

ACC ACT GTT CCA ACG ACA ACG ACC CTT CCA ACA ACA ACA ACC CTT CCA              663
```

|  |  |  |  |  |  |  |  |  |  |  |  |  |  |  |  |  |
|---|---|---|---|---|---|---|---|---|---|---|---|---|---|---|---|---|
| Thr | Thr | Val | Pro | Thr<br>145 | Thr | Thr | Thr | Leu | Pro<br>150 | Thr | Thr | Thr | Thr | Leu<br>155 | Pro | |
| ACG<br>Thr | ACA<br>Thr | ACG<br>Thr | ACT<br>Thr<br>160 | CTT<br>Leu | CCA<br>Pro | ACG<br>Thr | ACA<br>Thr | ACC<br>Thr<br>165 | CTT<br>Leu | CCA<br>Pro | ATG<br>Met | ACA<br>Thr<br>170 | ACG<br>Thr | ACT<br>Thr | | 711 |
| CTT<br>Leu | CCA<br>Pro | ATG<br>Met<br>175 | ACA<br>Thr | ACA<br>Thr | ACC<br>Thr | CTT<br>Leu | CCA<br>Pro<br>180 | ACT<br>Thr | ACA<br>Thr | ACG<br>Thr | ACT<br>Thr | GTT<br>Val<br>185 | CCA<br>Pro | ACG<br>Thr | ACA<br>Thr | 759 |
| ACG<br>Thr | ACC<br>Thr<br>190 | CTT<br>Leu | CCA<br>Pro | ACG<br>Thr | ACA<br>Thr | ACG<br>Thr<br>195 | ACT<br>Thr | CTT<br>Leu | CCA<br>Pro | ACG<br>Thr | ACT<br>Thr<br>200 | CTT<br>Leu | CCA<br>Pro | ATG<br>Met | ACA<br>Thr | 807 |
| ACG<br>Thr<br>205 | ACT<br>Thr | CTT<br>Leu | CCA<br>Pro | ACG<br>Thr | ACA<br>Thr<br>210 | AGG<br>Arg | ACT<br>Thr | CTT<br>Leu | CCA<br>Pro | ACG<br>Thr<br>215 | ACA<br>Thr | ACG<br>Thr | ACT<br>Thr | CTT<br>Leu | CCA<br>Pro<br>220 | 855 |
| ACG<br>Thr | ACA<br>Thr | ATG<br>Met | ACC<br>Thr | CTT<br>Leu<br>225 | CCA<br>Pro | ATG<br>Met | ACG<br>Thr | ACG<br>Thr | ACT<br>Thr<br>230 | CTT<br>Leu | CCA<br>Pro | ACG<br>Thr | ACG<br>Thr | ACG<br>Thr<br>235 | ACC<br>Thr | 903 |
| CTT<br>Leu | CCA<br>Pro | ACG<br>Thr | ACG<br>Thr<br>240 | ACG<br>Thr | ACC<br>Thr | CTT<br>Leu | CCA<br>Pro | ACG<br>Thr<br>245 | ACG<br>Thr | ACT<br>Thr | CTG<br>Leu | CCA<br>Pro | ACG<br>Thr<br>250 | ATG<br>Met | ACT<br>Thr | 951 |
| CTT<br>Leu | CCA<br>Pro | ACG<br>Thr<br>255 | ACA<br>Thr | ACG<br>Thr | ACT<br>Thr | CTT<br>Leu | CCA<br>Pro<br>260 | ACG<br>Thr | ATG<br>Met | ATG<br>Met | ACT<br>Thr | CTG<br>Leu<br>265 | CCA<br>Pro | ACG<br>Thr | ACA<br>Thr | 999 |
| ACA<br>Thr | ACT<br>Thr<br>270 | CTT<br>Leu | CCA<br>Pro | ACA<br>Thr | ACA<br>Thr | ACA<br>Thr<br>275 | ACT<br>Thr | CTG<br>Leu | CCA<br>Pro | ACG<br>Thr | ACA<br>Thr<br>280 | ACC<br>Thr | ATG<br>Met | GTT<br>Val | TCT<br>Ser | 1047 |
| ACC<br>Thr<br>285 | TTT<br>Phe | GTT<br>Val | CCT<br>Pro | CCA<br>Pro | ACA<br>Thr<br>290 | CCA<br>Pro | TTG<br>Leu | CCC<br>Pro | ATG<br>Met | CAG<br>Gln<br>295 | AAC<br>Asn | CAT<br>His | GAA<br>Glu | CCA<br>Pro | GTA<br>Val<br>300 | 1095 |
| GCC<br>Ala | ACT<br>Thr | TCA<br>Ser | CCA<br>Pro | TCT<br>Ser<br>305 | TCA<br>Ser | CCT<br>Pro | CAG<br>Gln | CCA<br>Pro | GCA<br>Ala<br>310 | GAA<br>Glu | ACC<br>Thr | CAC<br>His | CCT<br>Pro | GTG<br>Val<br>315 | ACA<br>Thr | 1143 |
| CTG<br>Leu | CTG<br>Leu | GGA<br>Gly | GCA<br>Ala<br>320 | ACA<br>Thr | AGG<br>Arg | ACA<br>Thr | CAA<br>Gln | CCC<br>Pro<br>325 | ACC<br>Thr | AGC<br>Ser | TCA<br>Ser | CCA<br>Pro | TTG<br>Leu<br>330 | TAC<br>Tyr | TCT<br>Ser | 1191 |
| TAC<br>Tyr | ACA<br>Thr | ACA<br>Thr<br>335 | GAT<br>Asp | GGG<br>Gly | AGT<br>Ser | GAC<br>Asp | ACC<br>Thr<br>340 | GTG<br>Val | ACA<br>Thr | GAG<br>Glu | TCT<br>Ser | TCA<br>Ser<br>345 | GAT<br>Asp | GGC<br>Gly | CTT<br>Leu | 1239 |
| TGG<br>Trp | AAT<br>Asn<br>350 | AAC<br>Asn | AAT<br>Asn | CAA<br>Gln | ACT<br>Thr | CAA<br>Gln<br>355 | TTG<br>Leu | TCC<br>Ser | CCA<br>Pro | GAA<br>Glu | CAT<br>His<br>360 | AGT<br>Ser | CCA<br>Pro | CAG<br>Gln | ATG<br>Met | 1287 |
| GTC<br>Val<br>365 | AAC<br>Asn | ACC<br>Thr | ACT<br>Thr | GAA<br>Glu | GGA<br>Gly<br>370 | ATC<br>Ile | TAT<br>Tyr | GCT<br>Ala | GGA<br>Gly | GTC<br>Val<br>375 | TGT<br>Cys | ATT<br>Ile | TCT<br>Ser | GTC<br>Val | TTG<br>Leu<br>380 | 1335 |
| GTG<br>Val | CTT<br>Leu | CTT<br>Leu | GCT<br>Ala | GTT<br>Val<br>385 | TTG<br>Leu | GGT<br>Gly | GTC<br>Val | GTC<br>Val | ATT<br>Ile<br>390 | GCC<br>Ala | AAA<br>Lys | AAG<br>Lys | TAT<br>Tyr | TTC<br>Phe<br>395 | TTC<br>Phe | 1383 |
| AAA<br>Lys | AAG<br>Lys | GAG<br>Glu | ATT<br>Ile<br>400 | CAA<br>Gln | CAA<br>Gln | CTA<br>Leu | AGT<br>Ser | GTT<br>Val<br>405 | TCA<br>Ser | TTT<br>Phe | AGC<br>Ser | AAC<br>Asn | CAT<br>His<br>410 | CAA<br>Gln | TTT<br>Phe | 1431 |
| AAA<br>Lys | ACT<br>Thr | TTG<br>Leu<br>415 | CAA<br>Gln | AAT<br>Asn | GCA<br>Ala | GTT<br>Val | AAA<br>Lys<br>420 | AAG<br>Lys | GAA<br>Glu | GTC<br>Val | CAT<br>His | GCA<br>Ala<br>425 | GAA<br>Glu | GAC<br>Asp | AAT<br>Asn | 1479 |
| ATC<br>Ile | TAC<br>Tyr | ATT<br>Ile<br>430 | GAG<br>Glu | AAT<br>Asn | AAT<br>Asn | CTT<br>Leu | TAT<br>Tyr<br>435 | GCC<br>Ala | ATG<br>Met | AAC<br>Asn | CAA<br>Gln | GAC<br>Asp<br>440 | CCA<br>Pro | GTG<br>Val | GTG<br>Val | 1527 |
| CTC<br>Leu | TTT<br>Phe<br>445 | GAG<br>Glu | AGT<br>Ser | TTA<br>Leu | CGC<br>Arg<br>450 | CCA<br>Pro | TGACTGCAGA | | AGACTGAACA | | TATCGGACGT | | | | | 1578 |
| CTTTGAGACT | | CCAAGACAAT | | TTTTCTGTTT | | CAGTTTCATC | | TGGCCTTCCA | | ACATGTCAGT | | | | | | 1638 |

```
GACACTGGGT AGAGTAACTC TCTTGCTCCA AACTGTGTAT AGTCAGCCTC ATCATTAATG    1698

TAGTCCTAAT TTTTTGTGCT AAAACAGGTT CAATCAATCC TTCTGATCAT TGTAGAGTTC    1758

TCTGTCAAAC ATGAACACTT TAGAATTGTA TGTTCTCTTT AGACCCCATA AATCCTGTAT    1818

CCATCAGAGA GAATAGTCAC TGGAAACATA GCAAATGAAC TTCTGTCTTG GCCATCAAAG    1878

CTGTGCAGAA GAGGGAAATC TGTCTTAAAA ATCAGCAAAT CCGATGTGAG ACTTCATTTG    1938

GAAGCATTAC ATGATAATCT CTTGTTTCTA TATGATACTT CCAAATGTTG CATTTCCTGT    1998

GTTTTCCAAA GGTTTCAAAT CATTGGGCTT TTAATTGCCT CCATGGGGAA ATAAAGTGAG    2058

TTTAATTCAC CCTAAAAAAA AAAAAAAAA AAAAA                                2093
```

( 2 ) INFORMATION FOR SEQ ID NO:2:

( i ) SEQUENCE CHARACTERISTICS:
        ( A ) LENGTH: 451 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  His  Leu  Gln  Val  Val  Ile  Leu  Ser  Leu  Ile  Leu  His  Leu  Ala  Asp
 1              5                        10                       15

Ser  Val  Ala  Asp  Ser  Val  Asn  Val  Asp  Gly  Val  Ala  Gly  Leu  Ser  Ile
               20                       25                       30

Thr  Leu  Pro  Cys  Arg  Tyr  Asn  Gly  Ala  Ile  Thr  Ser  Met  Cys  Trp  Asn
          35                       40                       45

Arg  Gly  Thr  Cys  Ser  Val  Phe  Ser  Cys  Pro  Asp  Gly  Ile  Val  Trp  Thr
     50                       55                       60

Asn  Gly  Thr  His  Val  Thr  Tyr  Arg  Lys  Glu  Thr  Arg  Tyr  Lys  Leu  Leu
 65                       70                       75                       80

Gly  Asn  Leu  Ser  Arg  Arg  Asp  Val  Ser  Leu  Thr  Ile  Ala  Asn  Thr  Ala
               85                       90                       95

Val  Ser  Asp  Ser  Gly  Ile  Tyr  Cys  Cys  Arg  Val  Lys  His  Ser  Gly  Trp
              100                      105                      110

Phe  Asn  Asp  Met  Lys  Ile  Thr  Ile  Ser  Leu  Lys  Ile  Gly  Pro  Pro  Arg
              115                      120                      125

Val  Thr  Thr  Pro  Ile  Val  Arg  Thr  Val  Arg  Thr  Ser  Thr  Thr  Val  Pro
     130                      135                      140

Thr  Thr  Thr  Thr  Leu  Pro  Thr  Thr  Thr  Thr  Leu  Pro  Thr  Thr  Thr  Thr
145                       150                      155                      160

Leu  Pro  Thr  Thr  Thr  Thr  Leu  Pro  Met  Thr  Thr  Thr  Leu  Pro  Met  Thr
                    165                      170                      175

Thr  Thr  Leu  Pro  Thr  Thr  Thr  Val  Pro  Thr  Thr  Thr  Thr  Leu  Pro
               180                      185                      190

Thr  Thr  Thr  Thr  Leu  Pro  Thr  Thr  Leu  Pro  Met  Thr  Thr  Thr  Leu  Pro
               195                      200                      205

Thr  Thr  Arg  Thr  Leu  Pro  Thr  Thr  Thr  Leu  Pro  Thr  Thr  Met  Thr
     210                      215                      220

Leu  Pro  Met  Thr  Thr  Thr  Leu  Pro  Thr  Thr  Thr  Leu  Pro  Thr  Thr
225                       230                      235                      240

Thr  Thr  Leu  Pro  Thr  Thr  Thr  Leu  Pro  Thr  Met  Thr  Leu  Pro  Thr  Thr
                    245                      250                      255

Thr  Thr  Leu  Pro  Thr  Met  Met  Thr  Leu  Pro  Thr  Thr  Thr  Leu  Pro
               260                      265                      270
```

| | | | | | | | | | | | | | | |
|---|---|---|---|---|---|---|---|---|---|---|---|---|---|---|
| Thr | Thr | Thr 275 | Thr | Leu | Pro | Thr | Thr 280 | Thr | Met | Val | Ser | Thr 285 | Phe | Val | Pro |
| Pro | Thr 290 | Pro | Leu | Pro | Met | Gln 295 | Asn | His | Glu | Pro | Val 300 | Ala | Thr | Ser | Pro |
| Ser 305 | Ser | Pro | Gln | Pro 310 | Ala | Glu | Thr | His | Pro 315 | Val | Thr | Leu | Leu | Gly | Ala 320 |
| Thr | Arg | Thr | Gln | Pro 325 | Thr | Ser | Ser | Pro | Leu 330 | Tyr | Ser | Tyr | Thr | Thr 335 | Asp |
| Gly | Ser | Asp | Thr 340 | Val | Thr | Glu | Ser | Ser 345 | Asp | Gly | Leu | Trp | Asn 350 | Asn | Asn |
| Gln | Thr | Gln 355 | Leu | Ser | Pro | Glu | His 360 | Ser | Pro | Gln | Met | Val 365 | Asn | Thr | Thr |
| Glu | Gly 370 | Ile | Tyr | Ala | Gly | Val 375 | Cys | Ile | Ser | Val | Leu 380 | Val | Leu | Leu | Ala |
| Val 385 | Leu | Gly | Val | Val | Ile 390 | Ala | Lys | Lys | Tyr | Phe 395 | Phe | Lys | Lys | Glu | Ile 400 |
| Gln | Gln | Leu | Ser | Val 405 | Ser | Phe | Ser | Asn | His 410 | Gln | Phe | Lys | Thr | Leu 415 | Gln |
| Asn | Ala | Val | Lys 420 | Lys | Glu | Val | His | Ala 425 | Glu | Asp | Asn | Ile | Tyr 430 | Ile | Glu |
| Asn | Asn | Leu 435 | Tyr | Ala | Met | Asn | Gln 440 | Asp | Pro | Val | Val | Leu 445 | Phe | Glu | Ser |
| Leu | Arg | Pro 450 | | | | | | | | | | | | | |

( 2 ) INFORMATION FOR SEQ ID NO:3:

( i ) SEQUENCE CHARACTERISTICS:
        ( A ) LENGTH: 303 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:3:

| | | | | | |
|---|---|---|---|---|---|
| AGAGAACTCA | GGAAGGCTCA | GGGTTATCCA | GCATTGTGAG | TGACAGAGCT | TGGATCTGAA | 60 |
| CGCTGATCCC | ATAATGCATC | TTCAAGTGGT | CATCTTAAGC | CTCATCCTAC | ATCTGGCAGA | 120 |
| TTCTGTAGCC | GATTCTGTAA | ATGTTGATGG | AGTGGCAGGT | CTATCTATCA | CACTGCCCTG | 180 |
| CCGCTACAAC | GGAGCTATCA | CATCCATGTG | CTGGAATAGA | GGCACATGTT | CTGTTTTCTC | 240 |
| ATGCCCAGAT | GGCATTGTCT | GGACCAATGG | AACCCACGTC | ACCTATCGGA | AGGAGACACG | 300 |
| CTA | | | | | | 303 |

( 2 ) INFORMATION FOR SEQ ID NO:4:

( i ) SEQUENCE CHARACTERISTICS:
        ( A ) LENGTH: 80 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:4:

| | | | | |
|---|---|---|---|---|
| CCGATTCTGT | AAATGTTGAT | GGAGTGGCAG | GTCTATCTAT | CACACTGCCC | TGCCGCTACA | 60 |
| ACGGAGCTAT | CACATCCATG | | | | | 80 |

( 2 ) INFORMATION FOR SEQ ID NO:5:

( i ) SEQUENCE CHARACTERISTICS:
    ( A ) LENGTH: 81 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:5:

```
TGCAGAAGAC AATATCTACA TTGAGAATAA TCTTTATGCC ATGAACCAAG ACCCAGTGGT    60
GCTCTTTGAG AGTTTACGCC C                                              81
```

RECOMBINANT DNA ENCODING HEPATITIS A VIRUS RECEPTOR

BACKGROUND OF THE INVENTION

1. Field of the Invention

The present invention relates to hepatitis A virus and to a cellular receptor for hepatitis A virus. Specifically, the invention relates to nucleic acids encoding the receptor polypeptide, to the receptor polypeptide, and to homologs of the cloned hepatitis A virus receptor. The invention also relates to methods for detecting, preventing and treating hepatitis A virus infection, methods of purifying and removing hepatitis A virus from samples, methods of determining the anti-hepatitis A virus activity of compounds, transgenic animals expressing a foreign gene encoding the hepatitis A virus receptor, and methods of vaccine testing utilizing the cloned hepatitis A virus receptor expressed in a transgenic animal.

2. Background Art

Hepatitis A virus (HAV), a member of the Picornavirus genera, is a nonenveloped virus ranging from 27 to 32 nm in diameter. The virion of HAV is composed of a genome of a linear, single-stranded RNA of 7,480 nucleotides and a capsid containing multiple copies of three or four proteins. The genome of HAV can be divided into three parts: (1) a 5' noncoding region; (2) a single open-reading frame that appears to encode all of the viral proteins, with regions designated as P1 for capsid proteins and P2 and P3 for nonstructural proteins; and (3) a short 3' noncoding region. Hepatitis A virus is relatively acid stable, heat resistant, and generally resistant to harsh environmental conditions (Sobsey, M. D., et al., (1988)).

Natural infection with HAV usually follows ingestion of material contaminated with feces containing HAV. The course of viral hepatitis is variable: in addition to subclinical cases, patients may develop icteric or anicteric (jaundice associated or non-jaundice associated, respectively) hepatitis. Symptoms for HAV infection may range from mild and transient to severe and prolonged for the later two subgroups. Patients with subclinical hepatitis have neither symptoms nor jaundice; their disease is recognized by detecting biochemical or serological alterations in their blood. The frequency of clinical disease increases with age. Anicteric hepatitis A infection occurs in over 90% of infected children under the age of 5, whereas only 25 to 50% of infected adults respond to HAV infection without symptoms of jaundice. In contrast, icteric disease (jaundice) is very common in adults who acquire HAV.

Hepatitis A virus occasionally causes acute liver disease in infected individuals. In these occasional acute viral hepatitis, extensive necrosis of the liver may occur which leads to severe impairment of hepatic synthesis processes, excretory functions, and detoxifying mechanisms. Symptoms of this infection pattern are characterized by the sudden onset of high fever, marked abdominal pain, vomiting, and jaundice, followed by the onset of hepatic encephalopathy associated with deep coma and seizures. Ascites and decerebrate rigidity may lead to death in 70 to 90% of these patients.

Although the natural infection route for HAV is fecal-oral, it is still unclear whether the virus is transported directly to the liver or whether it undergoes primary replication at sites earlier in the infection route. Identification of primary infection sites is important in the development of prevention and effective therapeutic strategies and development of successful vaccines.

Currently there is no small animal model for studying hepatitis A virus infection, tropism, or disease progression in a laboratory setting. Large animal models are available, the chimpanzee for example, but such models are inherently limiting and constitute a significant barrier to effectively studying hepatitis A virus disease and the development of therapies, drugs, or vaccines to treat or prevent hepatitis A virus disease. A need therefore exists to develop a small animal model to provide a valuable research tool for economically and effectively studying hepatitis A virus infection and disease.

The cellular receptor is the major determinant of cell and tissue tropism for HAV. Identification of the cellular receptor for HAV is therefore important for determining the sites of primary infection and tissue tropism. Despite the known pathogenicity of HAV and the urgency of the development of a successful vaccine against HAV infection, a cellular receptor for HAV has not been identified in the art. Previous studies have only partially characterized various biochemical aspects of hepatitis A virus binding proteins, such as calcium dependency (Stapleton, J. T., et al., (1991)), the binding co-operativity of HAV to a HAV binding protein (Collier, A. J. and Wolstenholme, A. J. (1994)), and cell surface susceptibility of HAV attachment (Seganti, L., et al., (1987)). Anderson, et al., (abstract NO. P5-1 to the Third International Symposium on Positive Strand RNA Viruses, held in Clearwater, Fla. from Sep. 19 to Sep. 24, 1992) describes a protein stated to bind hepatitis A virus. Anderson, et al. states that HAV binds to a cell surface protein of molecular weight between 100,000 and 200,000 daltons. However, this protein is not a hepatitis A virus receptor. Thus, despite the need for a purified hepatitis A virus receptor, there has been no success.

Therefore a need exists to identify the cellular receptor for hepatitis A virus and to provide methods for diagnosing, treating, and preventing hepatitis A virus infection. Likewise, a need exists for methods for purifying and/or removing hepatitis A virus from samples, and for determining the anti-HAV binding activity of compounds. There also exists a need for the nucleotide sequence encoding the hepatitis A virus receptor and for transgenic animals expressing the exogenous hepatitis A virus receptor gene in order to effectively study the route of HAV infection and to develop successful vaccines to prevent against, or treatments for, HAV infection.

SUMMARY OF THE INVENTION

The present invention provides the discovery and isolation of a cellular receptor for hepatitis A virus. This receptor has the biological activity of transforming cells previously nonpermissive for hepatitis A virus infection into cells permissive for hepatitis A virus infection. Purified polypeptides comprising all or part of the HAV receptor are also provided by the present invention. These polypeptides can be utilized to diagnose infection by hepatitis A virus, to separate hepatitis A virus from impurities in a sample, to treat infection, as well as prevent infection by hepatitis A virus. Polypeptides of the present invention can be expressed in a transformed cell and utilized to test the efficacy of compounds in an anti-hepatitis A virus binding assay.

The present invention also provides an isolated nucleic acid molecule comprising a nucleic acid encoding a polypeptide having the biological activity of a hepatitis A virus receptor. An isolated nucleic acid that hybridizes with the HAV receptor-encoding nucleic acid under the specified stringency conditions is also provided. The isolated nucleic acids of the present invention can be utilized to express the hepatitis A virus receptor, or active fragments thereof, and to diagnose infection by hepatitis A virus. This is the first identification of a hepatitis A virus receptor polypeptide and the first cloning of a nucleic acid encoding a polypeptide which has the biological activity of a hepatitis A virus receptor.

The present invention also provides vectors comprising the isolated nucleic acids encoding a hepatitis A virus receptor or fragments thereof. These vectors can be utilized for expression of the nucleic acids in host expression systems to produce the entire hepatitis A virus receptor or fragments of the receptor, including functional domains of the receptor.

Further provided by the present invention is a nonhuman transgenic animal which expresses a hepatitis A virus receptor of the present invention, but does not express an endogenous, active HAV receptor. The present invention also comprises using the transgenic animal as a test model for testing the efficacy of hepatitis A virus vaccines, as well as other therapies designed to prevent infection and treat infection by hepatitis A virus. The transgenic animal, which is susceptible to HAV infection, can also be used to generate large quantities of HAV.

DETAILED DESCRIPTION OF THE INVENTION

Purified Hepatitis A Virus Receptor

Figure 1:
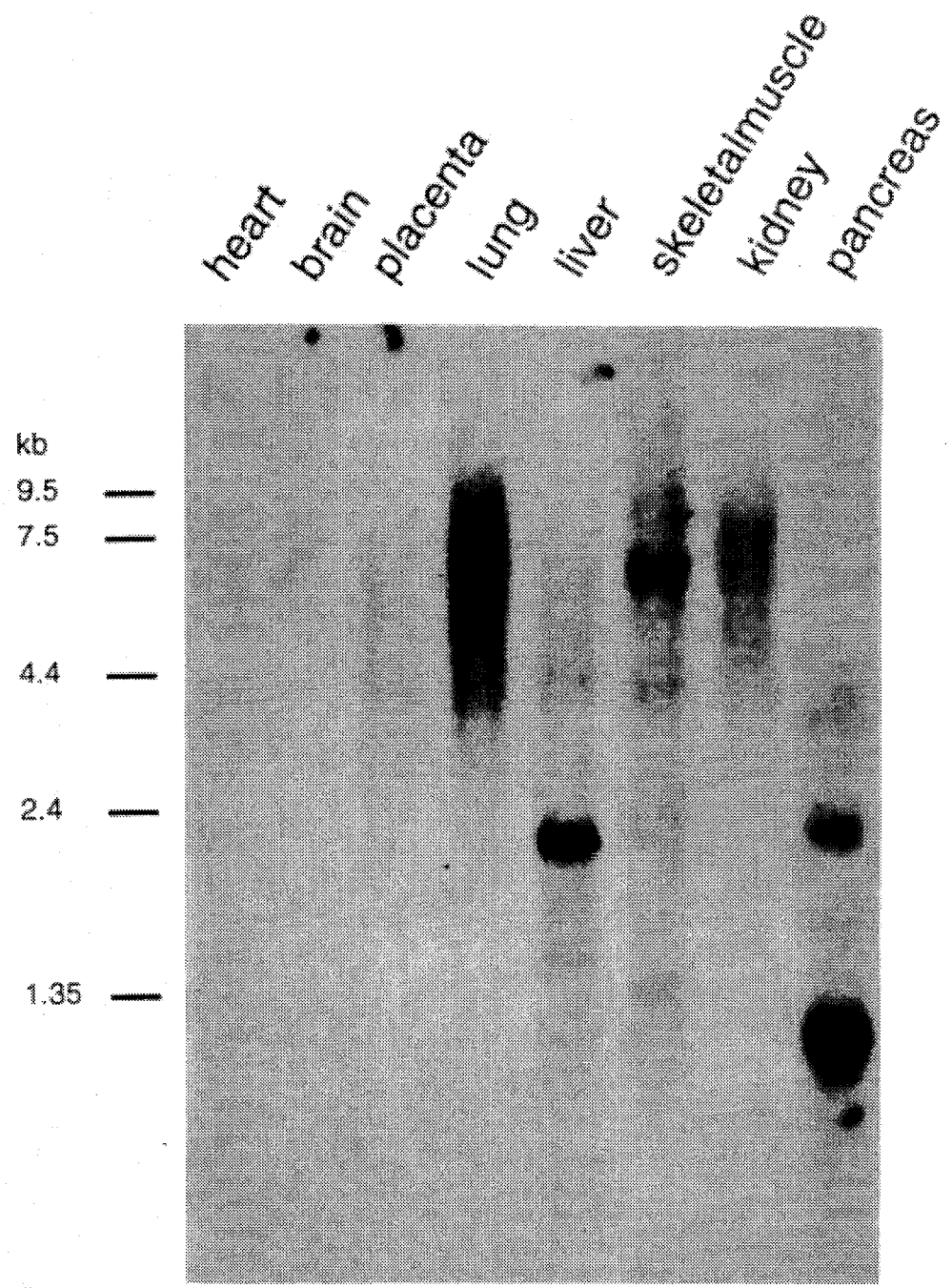
FIG. 1 shows a Northern blot of poly A+RNAs from various tissues probed with a fragment of the nucleic acid set forth in the Sequence Listing as SEQ ID NO: 1.

The present invention provides a purified hepatitis A virus receptor consisting of the polypeptide set forth in the Sequence Listing as SEQ ID NO: 1. By "purified" is meant more pure than the compound exists in nature and pure enough for use in an assay, e.g., more pure than a cellular extract containing the receptor. This definition contemplates a polypeptide that is essentially free of normally present cellular components such as nucleic acids not part of the gene for the polypeptide, and cellular structures. An example of a purified polypeptide of the invention is a HAV receptor in a protein extract from a cell that does not normally express the receptor, but has been transfected or transformed to express the receptor or is from a transgenic animal as described below. Another example of a purified polypeptide is an in vitro synthesized polypeptide, obtained using a cell-free translation system or a linked transcription-translation system. Direct synthesis is also a method of obtaining a purified receptor or fragment of the invention. Purification of the receptor or fragment produced by any method can be accomplished by a number of routine methods and combinations of methods such as electrophoresis, blotting, precipitation, immunoprecipitation, dialysis, chromatography or combinations of these and other methods.

The present invention also provides for a purified homolog of the hepatitis A virus receptor consisting of the polypeptide set forth in the Sequence Listing as SEQ ID NO: 1. Such homolog may be obtained from a human or other primate species whose genome encodes a homolog of the present hepatitis A virus receptor. For instance, the Example provides a hybridization assay in which a human homolog of the receptor of SEQ ID NO: 1 was detected. Methods used to isolate a nucleic acid encoding a human or other homolog to the purified hepatitis of SEQ ID NO: 1 include, but are not limited to, screening the genome of a species believed to encode a hepatitis A virus homolog by nucleic acid hybridization methods or through polymerase chain reaction (PCR) techniques. Materials suitable for screening include, but are not limited to, cDNA or genomic libraries of the appropriate animal cloned into lambda, cosmid, yeast, mammalian, or plasmid cloning vectors, DNA isolated and subjected to Southern blot analysis, RNA isolated and subjected to Northern blot analysis, and isolated DNA or RNA used as a template for PCR. An example of a homolog of the receptor of SEQ ID NO: 1 is the selectively hybridizing nucleic acid described below, which encodes the human HAV receptor.

The invention provides purified polypeptide fragments of the HAV receptor that have virus binding activity. Fragments including those encoded by the nucleic acids of the present invention are also contemplated. The polypeptide fragments of the present invention can be recombinant proteins obtained by cloning nucleic acids encoding the polypeptide in an expression system capable of producing the polypeptide or fragments thereof. The purified hepatitis A virus binding domain can be used in drug screening, purification of hepatitis from a sample, detection of hepatitis A virus in a sample, and other assays as described below.

The invention also provides purified polypeptide fragments of the HAV receptor that regulate virus binding activity at a virus binding domain of the hepatitis A virus receptor. Fragments including those encoded by the nucleic acids of the present invention are also contemplated. The polypeptide fragments of the present invention can also be recombinant proteins obtained by cloning nucleic acids encoding the polypeptide in an expression system capable of producing the polypeptide or fragments thereof. The purified hepatitis A virus receptor regulatory domain can be utilized in a system to regulate the binding activity of endogenous hepatitis A virus receptors, in a research setting to investigate the method of regulation of hepatitis A binding proteins, or as a model to investigate the regulation of ligand binding proteins.

The purified polypeptides can be tested to determine their activity and specificity by the methods taught herein. Active fragments of the polypeptide can also be synthesized directly or obtained by chemical or mechanical disruption of larger polypeptides. An active fragment is defined as an amino acid sequence of at least about 5 consecutive amino acids derived from the naturally occurring amino acid sequence, which has the relevant activity, e.g., binding or regulatory activity.

Once the amino acid sequence of the polypeptide is provided, it is also possible to synthesize, using standard peptide synthesis techniques, peptide fragments chosen to be homologous to active regions of the receptor. Fragments of the HAV receptor possessing an activity of the receptor can be obtained by mechanical or chemical disruption of the receptor protein, followed by fractionation. Thus, synthesis or purification of an extremely large number of fragments derived from the polypeptide is possible.

The entire polypeptide or fragments can be attached to sequences designed to provide for some additional property, such as solubility. The fragments, whether attached to other sequences or not, can also include insertions, deletions, substitutions, or other selected modifications of particular regions or specific amino acids residues, provided the activity of the peptide is not significantly altered or impaired compared to the native polypeptide or fragment thereof. These modifications to a fragment of the HAV receptor can provide for some additional property, such as to remove/add amino acids capable of disulfide bonding, to increase its bio-longevity, etc. In any case, the peptide must possess a bioactive property, such as binding activity, regulation of binding at the binding domain, etc. Functional or active regions of the hepatitis A virus receptor may be identified by mutagenesis of a specific region of the receptor, followed by expression and testing of the expressed polypeptide. Such methods are readily apparent to a skilled practitioner in the art and can include site-specific mutagenesis of the nucleic acid encoding the receptor. (Zoller, M. J. and Smith, M. Oligonucleotide-directed mutagenesis using M13-derived vectors: an efficient and general procedure for production of point mutations in any fragment of DNA. Nuc. Acids Res. 10: 6487–6500 (1982)).

The invention also provides the purified hepatitis A virus receptor or fragment (e.g., binding domain or regulatory domain) bound to a solid support. Examples of suitable substrates include, but are not limited to, polymers, beads (e.g., agarose, polystyrene, sepharose, etc.), latex plates, glass or plastic petri or culture dishes, albumin, and the like. Other suitable substrates can be selected by referring to standard references, e.g., Harlow and Lane, Antibodies: A Laboratory Manual, Cold Spring Harbor Laboratory, Cold Spring Harbor, N.Y., (1988).

Uses contemplated for this immobilized HAV receptor include, but are not limited to, affinity chromatography techniques such as those used to concentrate specific molecules which bind to the receptor, in this example, HAV. The immobilized receptor can be used to identify other natural or artificial ligands. Techniques used to determine the concentration of HAV in a sample, such as enzyme linked immunosorbent assay and techniques used to purify HAV from contaminants in a sample comprising contacting the sample with immobilized HAV receptor followed by removing the immobilized HAV receptor and the HAV bound to the receptor from the sample, thereby purifying the HAV from the impurities in the sample are provided. Assays used to determine the effect specific compounds have on the ability of HAV to bind to a HAV receptor are also provided as described below.

Nucleic Acids

The present invention provides an isolated nucleic acid comprising the nucleic acid encoding the purified hepatitis A virus receptor consisting of the polypeptide set forth in the Sequence Listing as SEQ ID NO: 1. This nucleic acid can be the nucleic acid set forth in the Sequence Listing as SEQ ID NO: 1. The DNA sequence shown in SEQ ID NO: 1 is a 2093 nucleic acid encoding the polypeptide set forth in the Sequence Listing as SEQ ID NO: 1. The nucleic acid can be any other sequence of nucleotides that encodes the polypeptide set forth in the Sequence Listing as SEQ ID NO: 1. The nucleic acids of the invention can be double-stranded or can be in denatured (single-stranded) form. The invention includes DNA having the recited sequences and its complement, and RNAs which correspond to the DNA.

Also prodded is a nucleic acid that encodes a polypeptide comprising the HAV receptor binding domain or fragment of the receptor having binding activity. Also provided is a nucleic acid that encodes a polypeptide comprising HAV receptor regulatory domains or fragment of the receptor having regulatory activity. Such regulatory domains can be manipulated through recombinant techniques well known in the art to alter their activity and or effect on other regions of a hepatitis A virus receptor. Similarly, such regulatory regions may also be manipulated through recombinant techniques well known in the art to alter their activity and/or effect on other regions of a hepatitis A virus receptor or a hepatitis A virus binding domain.

By "isolated nucleic acid" is meant essentially separated from other genes and cellular material found in the organism. The nucleic acids of the present invention can include positive and negative strand RNA as well as DNA and includes genomic and subgenomic nucleic acids present in an organism. The nucleic acids contemplated by the present invention include a cDNA encoding the HAV receptor, the genomic DNA fragment containing the relevant introns and exons, as well as any upstream or downstream regulatory regions, the mRNA encoded by either the cDNA or the genomic DNA, and any nucleic acid which can hybridize to or encode the HAV receptor.

The present invention also provides isolated nucleic acid encoding a HAV receptor or functional fragment thereof that selectively hybridizes with the nucleic acid set forth in the Sequence Listing as SEQ ID NO: 1 or its complement. For example, an isolated nucleic acid that selectively hybridizes the nucleic acid set forth in SEQ ID NO: 1 under hybridization stringency conditions of 45° C., 50% formamide, and 5X SSC (1X SSC=8.765 grams Sodium Chloride and 4.410 grams Sodium Citrate in a volume of 1 liter of $H_2O$, pH 7.0), followed by washing stringency conditions of 65° C. and 0.2X SSC and 0.1% SDS (sodium dodecyl sulfate) is provided. Alternatively, an isolated nucleic acid that selectively hybridizes the nucleic acid set forth in SEQ ID NO: 1 under hybridization stringency conditions of 42° C., 50% formamide, 5X SSC with washing stringency conditions of 65° C., 2X SSC and 0.1% SDS or hybridization stringency conditions of 42° C., 5X SSPE (1X SSPE=8.765 grams Sodium Chloride, 1.380 grams Monosodium Phosphate ($NaH_2PO_4$, and 0.370 grams Disodium Ethylenediaminetetraacetate (EDTA) in a volume of 1 liter, pH 7.4) with washing stringency conditions of 42° C., 2X SSC and 0.1% SDS.

As used herein to describe nucleic acids, the term "selectively hybridizes" excludes the occasional randomly hybridizing nucleic acids. The selectively hybridizing nucleic acids can be used, for example, as probes or primers for detecting the presence of the hepatitis A virus receptor coding gene or messenger RNA provided in SEQ ID NO: 1, or a homolog thereof, that has the nucleic acid to which the primer or probe hybridizes.

The selectively hybridizing nucleic acids of the invention can have at least 60%, 70%, 80%, 85%, 90%, 95%, 97%, 98% and 99% complementarity with the segment of the sequence to which it hybridizes. The nucleic acids can be at least 12 to 4000 nucleotides in length. Thus, the nucleic acid can be a coding sequence for the hepatitis A virus receptor of SEQ ID NO: 1 or a homolog thereof or a functional fragment, or it can be used as a probe or primer for detecting the presence of the receptor. If used as primers, the invention provides compositions including at least two nucleic acids which selectively hybridize with different regions of the target nucleic acid so as to amplify a desired region. Depending on the length of the probe or primer, the target region can range between 70% complementary bases and full complementarity and still hybridize under the stringency conditions described herein.

For example, for the purpose of detecting the presence of the hepatitis A virus receptor, the degree of complementarity between the hybridizing nucleic acid (probe or primer) and the sequence to which it hybridizes (DNA or RNA from a sample) is at least enough to exclude significant hybridization with a nucleic acid from unrelated (nonhomologous) receptors or unrelated HAV binding proteins. By "significant hybridization" is meant that a hybridization assay can distinguish between the hepatitis A virus receptor of the present invention or a homolog to the hepatitis A virus receptor and a nucleic acid from a nonhomologous gene or polynucleotide. Thus, a nucleic acid that selectively hybridizes with a hepatitis A virus receptor sequence (as set forth in SEQ ID NO: 1) will not selectively hybridize, under the stringency conditions described herein, with a nucleic acid of a segment of another, nonhomologous receptor, and vice versa.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization (Kunkel et al., Methods Enzymol. 154: 367 (1987)).

The nucleic acids described herein can be used to detect the nucleic acid of the present invention in samples by methods such as the polymerase chain reaction, ligase chain reaction, hybridization, and the like. Alternatively, these sequences can be utilized to produce an antigenic protein or protein fragment, or an active protein or protein fragment.

In addition, fragments of the nucleic acids described herein can be selected to selectively or specifically hybridize with homologous nucleic acids present in other animals or humans. Such a nucleotide sequence shared with other organisms can be used, for example, to simultaneously detect related sequences for cloning of homologs of the nucleic acid of the present invention encoding a hepatitis A virus receptor polypeptide.

An isolated nucleic acid capable of selectively amplifying any region of the HAV receptor gene of the present invention is contemplated. The selectively hybridizing nucleic acids would not selectively hybridize with the nucleic acids of other presently known picornavirus receptors, such as the poliovirus receptor (Mendelsohn, C. L., et al., Cellular receptor for poliovirus: molecular cloning, nucleotide sequence, and expression of a new member of the immunoglobulin superfamily. Cell 56: 855–865 (1989)). Available computer programs can be used to compare the sequence to select the most appropriate sequences for amplification palmers and hybridization probes.

Virus Detection (Diagnosis) Methods

The invention provides a method of detecting the presence of hepatitis A virus in a sample, comprising contacting the purified hepatitis A virus receptor with a sample and detecting the presence of binding of hepatitis A virus to the purified receptor, the presence of binding indicating the presence of hepatitis A virus in the sample. For example, the purified hepatitis A virus receptor comprising the polypeptide set forth in the Sequence Listing as SEQ ID NO: 1 can be utilized in a method to determine the presence of hepatitis A virus in a sample. A fragment of the receptor that has HAV binding activity, for example a binding domain, can also be used to bind, and thus, detect HAV in a sample. As contemplated herein, purified receptor fragments include any portion of the receptor which binds hepatitis A virus.

One example of a method of detecting hepatitis A virus in a sample is performed by contacting a fluid or tissue sample from a subject with an amount of purified hepatitis A virus receptor or a binding domain of a hepatitis A virus receptor and detecting the binding of the receptor with the virus or an empty capsid of the virus. The fluid sample of this method can comprise any body fluid which would contain the virus or a cell containing the virus, such as, but not limited to, blood, plasma, serum, saliva, semen, feces, or urine. Other possible examples of body fluids include sputum, mucus, gastric juice, and the like. The tissue sample of this method can comprise any tissue obtained from a subject or patient, such as, but not limited to, brain tissue, liver tissue, kidney tissue, heart tissue, lung tissue, placenta tissue, skin tissue, muscle tissue, pancreatic tissue, and so forth. Such tissue samples can be prepared for analysis by disruption and separation into fractions based on size or density, or lysed for analysis of the cellular extracts. Other methods for tissue preparation are common and obvious to a skilled practitioner in the relevant art.

In one embodiment of the present HAV detection method, the presence of binding is determined by an immunoassay. Immunoassays such as immunofluorescence assays (IFA), enzyme linked immunosorbent assays (ELISA), and immunoblotting assays can be readily adapted to accomplish the detection of the HAV bound to the receptor. An ELISA method effective for the detection of the virus can, for example, be as follows: (1) bind the receptor to a substrate; (2) contact the bound receptor with a fluid or tissue sample containing the virus; (3) contact the above with a specific antibody bound to a detectable moiety (e.g., horseradish peroxidase enzyme or alkaline phosphatase enzyme); (4) contact the above with the substrate for the enzyme; (5) contact the above with a color reagent; and (6) observe color change. The above method can be readily modified to detect presence of the receptor as well as the virus.

Another immunologic technique that can be useful in the detection of HAV is a competitive inhibition assay wherein hepatitis A virus can be detected by competitive inhibition of receptor utilizing monoclonal antibodies (MABs) specifically reactive with the receptor. Briefly, sera or other body fluids from the subject is reacted with the receptor bound to a substrate (e.g. an ELISA 96-well plate). Excess sera is thoroughly washed away. A labeled (enzyme-linked, fluorescent, radioactive, etc.) monoclonal antibody is then reacted with the previously reacted hepatitis A virus-receptor complex. The mount of inhibition of monoclonal antibody binding is measured relative to a control. MABs can also be used for detection directly in samples by IFA for MABs specifically reactive for the receptor-virus complex.

Alternatively, a hepatitis A virus and/or a patient's antibodies to the virus can be detected utilizing a capture assay. Briefly, to detect antibodies to hepatitis A virus in a patient sample, antibodies to the patient's immunoglobulin, e.g., anti-IgG (or IgM) are bound to a solid phase substrate and used to capture the patient's immunoglobulin from serum. A hepatitis A virus, or reactive fragments of a hepatitis A virus, are then contacted with the solid phase followed by addition of a labeled receptor. The mount of patient hepatitis A virus specific antibody can then be quantitated by the amount of labeled receptor binding.

Additionally, a micro-agglutination test can also be used to detect the presence of hepatitis A virus in test samples. Briefly, latex beads are coated with the receptor and mixed with a test sample, such that hepatitis A virus in the tissue or body fluids that are specifically reactive with the receptor crosslink with the receptor, causing agglutination. The agglutinated receptor-virus complexes form a precipitate, visible with the naked eye or detectable by a spectrophotometer.

In the diagnostic methods described above, the sample can be taken directly from the patient or in a partially purified form. The receptor specific for hepatitis A virus reacts by binding the virus (the primary reaction). Thereafter, a secondary reaction with an anti-HAV antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the receptor or the virus will be selected for its ability to react with multiple sites on the complex of receptor and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, Antibodies: A Laboratory Manual, Cold Spring Harbor Laboratory, Cold Spring Harbor, N.Y., (1988)).

The bound hepatitis A virus receptor or binding domain of the hepatitis A virus receptor of the present invention can be used to detect the presence of a hepatitis A virus specifically reactive with the hepatitis A virus receptor or a reactive fragment thereof. One skilled in the art can also appreciate that the hepatitis A virus bound to a solid support of the present invention can also be designed for virus neutralization testing and/or capture immunoassays in the methods described herein for removal/purification of hepatitis A virus.

Prevention and Treatment Methods

One embodiment of the present invention is a method of treating a subject infected with hepatitis A virus, comprising administering to the subject a therapeutically effective amount of a purified hepatitis A virus receptor and a pharmaceutically acceptable carrier. In this method, the hepatitis A virus receptor can be the receptor comprising the polypeptide set forth in the Sequence Listing as SEQ ID NO: 1.

Another embodiment provided for by the present invention is a method of preventing in a subject hepatitis A virus infection, comprising administering to the subject a prophylactically effective amount of a purified hepatitis A virus receptor and a pharmaceutically acceptable carrier. The hepatitis A virus receptor can be the receptor comprising the polypeptide set forth in the Sequence Listing as SEQ ID NO: 1.

In a specific embodiment, the present invention provides a hepatitis A virus receptor or a binding domain of a hepatitis A virus receptor, in a pharmaceutically acceptable carrier in an amount sufficient to administer to a human to prevent or treat an infection by hepatitis A virus. Treatment or prevention &hepatitis A virus infection can be facilitated by competitive inhibition &hepatitis A virus binding to a cell by administration of exogenous hepatitis A virus receptor or a binding domain of a hepatitis A virus receptor in a pharmaceutically acceptable carrier. The amount of hepatitis A virus receptor or a binding domain of a hepatitis A virus receptor that would be sufficient to treat a hepatitis A virus infection in a human depends on the amount of hepatitis A virus receptor or a binding domain of a hepatitis A virus receptor on the cells of the human subject. The dose can be determined by optimization procedures. The amount of hepatitis A virus receptor or a binding domain of a hepatitis A virus receptor will also vary depending upon the weight, size, and health of the human subject, and with the severity of hepatitis A virus infection.

In addition, given the discovery of the nucleic acid encoding a hepatitis A virus receptor as a cellular receptor for hepatitis A virus, antagonists which specifically bind to a hepatitis A virus receptor or a binding domain of a hepatitis A virus receptor and antagonize the binding of hepatitis A virus are also provided. The antagonist can be an antibody or a chemical which binds the receptor or otherwise alters the receptor or interferes with the interaction of virus and receptor. For example, utilizing methods taught in the Examples and other methods known in the art, one can select a chemical which reacts with the binding site of the hepatitis A virus receptor or a binding domain of a hepatitis A virus receptor to antagonize binding of hepatitis A virus. Empty hepatitis A virus capsids can be utilized as the antagonist. Alternatively, anti-idiotype and anti-anti-idiotype antibodies to both a hepatitis A virus receptor or a binding domain of a hepatitis A virus receptor and the hepatitis A virus can be utilized for prophylaxis or therapy. Naturally, the treatment modality can be selected to minimize any adverse side effects such as immune system recognition and deletion of the desirable hepatitis A virus receptor expressing cells. Thus, the invention also provides a method of screening for compounds which antagonize the binding of hepatitis A virus.

An embodiment of the present invention is a method of determining the anti-hepatitis A virus binding activity of a compound, comprising contacting the purified hepatitis A virus receptor with the compound and with hepatitis A virus and determining the relative amount of hepatitis A virus bound to the receptor, the relative amount of virus bound to the receptor being an indication of the anti-hepatitis A virus binding activity of the compound. The hepatitis A virus receptor can be on a cell which expresses the receptor. The hepatitis A virus receptor can be the receptor comprising the polypeptide set forth in the Sequence Listing as SEQ ID NO: 1.

Depending on whether the compound selected by the screening method is administered orally, parenterally, or otherwise, the compounds of the present invention can be in pharmaceutical compositions in the form of solid, semi-solid, or liquid dosage forms, such as, for example, tablets, pills, capsules, powders, liquids, and suspensions, or the like, preferably in unit dosage form suitable for delivery of a precise dosage. The compositions will include, as noted above, an effective amount of the selected compound in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. Actual methods of preparing such dosage forms are known, or will be apparent, to those skilled in this art; for example, see *Remington's Pharmaceutical Sciences*, latest edition (Mack Publishing Co., Easton, Pa.).

Patients can also be treated orally with compositions of a hepatitis A virus receptor or a binding domain of a hepatitis A virus receptor to block infection from hepatitis A virus or to block transmission of hepatitis A virus. For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Also provided by the present invention is a method of preventing or treating hepatitis A virus infection in a human subject comprising preventing the binding of hepatitis A virus to a hepatitis A virus receptor or a binding domain of a hepatitis A virus receptor or other ligand by administering to the subject a composition comprising a hepatitis A virus receptor or a binding domain of a hepatitis A virus receptor which blocks the binding of hepatitis A virus to a hepatitis A virus receptor, binding domain, or natural ligand, thereby preventing or treating infection by the hepatitis A virus in the subject. As previously stated, the amount of the hepatitis A virus receptor or hepatitis A virus binding domain used in the method will depend upon many factors including the route of administration, relative potency of the composition and size and health of the patient. It is contemplated herein that a hepatitis A virus receptor or a binding domain of a hepatitis A virus receptor, or any portion of a hepatitis A virus receptor or binding domain of a hepatitis A virus receptor molecule reactive with hepatitis A virus can be utilized in the method to treat or prevent infection by hepatitis A virus.

Hepatitis A virus infection can also be prevented or treated by administering to the subject an antibody or other ligand reactive with a hepatitis A virus receptor or binding domain of other purified receptors which blocks the hepatitis A virus binding domain. The amount of antibody administered will also be dependent upon the mount of hepatitis A virus receptor on the cells of the subject and can be determined by optimization procedures as discussed herein.

By utilizing methods of identification and purification of the receptor taught herein, one skilled in the art can identify other hepatitis A virus receptors which can be utilized to prevent or treat hepatitis A virus infections in other species. For example, the purified receptor for chimpanzee hepatitis A virus can be utilized in a composition to prevent or treat infection or to block transmission of the virus in a chimpanzee utilizing methods for preparing the composition and optimization procedures for therapy described herein.

The present invention also provides a hepatitis A virus capable of infecting cells which express a hepatitis A virus receptor or binding domain of a hepatitis A virus receptor, wherein the hepatitis A virus has a human derived gene inserted into the hepatitis A virus genome. As a result of the discovery of the hepatitis A virus receptor, one skilled in the art can readily appreciate that hepatitis A virus or an attenuated strain can be utilized as a vector system to deliver hepatitis A virus to hepatitis A virus receptor expressing cells. Such methods are well known in the art and can be utilized by established procedures. (Sambrook et al., *Molecular Cloning: A Laboratory Manual*, 2nd Ed., Cold Spring Harbor Laboratory, Cold Spring Harbor, N.Y., (1989)).

Also provided is a method of introducing a therapeutant into a cell, comprising a therapeutant linked to or packaged within a hepatitis A virus capable of binding to the hepatitis A virus receptor or binding domain of a hepatitis A virus receptor of the present invention. A therapeutically effective amount of the therapeutant described above comprising the therapeutant and a pharmaceutically acceptable carrier discussed herein is contemplated. Such therapeutants comprise antibodies directed toward hepatitis A virus or a hepatitis A virus receptor or a binding domain of a hepatitis A virus receptor, drugs, compounds, or substances which may alter the binding of hepatitis A virus to a hepatitis A virus receptor or a binding domain of the hepatitis A virus receptor, fragments of a hepatitis A virus which bind to a hepatitis A virus receptor or a binding domain of a hepatitis A virus receptor, other natural or synthetic ligands which bind to a hepatitis A virus receptor or a binding domain of a hepatitis A virus receptor linked to a drug, compound, or other substance, or antibodies to a hepatitis A virus receptor or binding domain of a hepatitis A virus receptor linked to a drug, compound, or other substance.

Method of Producing HAV

The present invention also provides cells manipulated to have levels of hepatitis A virus receptor expressed on the cell surface which are increased over non-manipulated cells. The cells contemplated herein can be manipulated to contain increased levels of hepatitis A virus receptor or binding domain of hepatitis A virus or fragments thereof which act as a receptor for hepatitis A virus. One skilled in the art can appreciate that these cells can be manipulated in many ways including direct addition of hepatitis A virus receptor or binding domain of hepatitis A virus to cells with subsequent incorporation by mass action into the lipid bilayer of the cell. The manipulated cells of the present invention can include cells originally non-permissive for hepatitis A virus infection as well as permissive cells made more permissive. Examples of such cells include, but are not limited to, lymphocytes, hematopoietic stem cells or tumor cells.

Also provided by the present invention are cells expressing a foreign gene encoding a hepatitis A virus receptor or a binding domain of a hepatitis A virus receptor. Such cells include prokaryotic cells such as *E. coli*, or eukaryotic cells, such as COS-1 cells. Foreign genes can be introduced into these cells in a number of techniques, including, but not limited to, transfection, transformation, electroporation, injection, microinjection, and the like. Specifically, transfection includes techniques such as calcium phosphate coprecipitation, DEAE-Dextran mediated transfection, and lipofection. Viral vectors may also be utilized to introduce foreign genes into host cells. Cells expressing the foreign gene may therefore express the polypeptide encoded by the foreign gene on the cell surface. Such cells may therefore be infectable by hepatitis A virus and utilized either as models for studying infection of cells by hepatitis A virus, or as cells producing hepatitis A virus post-infection. A preferred embodiment of the present invention is a cell expressing the gene encoded by the sequence set forth in the Sequence Listing as SEQ ID NO: 1.

Augmentation of Virus Vector Efficiency

The invention provides a method of delivering a desired gene into a cell expressing the hepatitis A virus receptor or binding domain of hepatitis A virus comprising infecting the cell with a non-virulent (modified) hepatitis A virus having the desired gene inserted into the hepatitis A virus genome. The present invention also provides a method of augmenting the above method, comprising increasing the amount of hepatitis A virus receptor or binding domain of hepatitis A virus expressed on the cell surface and infecting the cell with a hepatitis A virus having the desired gene inserted into the hepatitis A virus genome. One skilled in the art will readily appreciate that the identification of hepatitis A virus receptor, as taught by the present invention, enables methods of gene therapy with hepatitis A virus as the vector system. The desired human DNA fragment can be easily inserted into a host cell, e.g., one with sufficient levels of hepatitis A virus receptor or binding domain of hepatitis A virus on the cell surface as discussed herein utilizing methods known in the art, for example, See, Nienhuis, A. W., et al., Marcel Dekker, New York (1993).

Purification of HAV from a Sample

Another embodiment of the present invention provides a method of separating a hepatitis A virus from impurities in a sample, comprising binding hepatitis A virus with a purified hepatitis A virus receptor or binding domain of hepatitis A virus and separating the bound hepatitis A virus from the unbound impurities in the sample, thereby separating the hepatitis A virus from impurities in the sample. A preferred embodiment of the present invention is where the hepatitis A virus receptor is the receptor comprising the polypeptide set forth in the Sequence Listing as SEQ ID NO: 1. One skilled in the art will appreciate, based on the teaching herein, that purification of hepatitis A virus can be accomplished by the use of immobilized receptor, or receptor fragments that specifically bind the target hepatitis A virus. Once a complex of receptor and virus is formed, the impurities in a sample can be separated using techniques well known in the art and set forth herein, such as column purification and centrifugation.

Removal of HAV from Blood

The present invention provides a method for removing HAV from a blood sample comprising binding the HAV in the blood with a purified receptor for the virus or an active HAV binding fragment thereof and separating the bound virus from the blood, thereby removing the HAV from the blood sample. Donated blood contaminated with HAV presents a health hazard. The method of the present invention utilizes the receptor for HAV, e.g., the receptor of SEQ ID NO: 1 or homologs thereof, to bind to the virus. The bound complex can be removed from the blood sample by preparing a column with the immobilized receptor. The sample is then passed through the column, thereby removing HAV from the sample utilizing the binding affinity of HAV for the receptor. Alternatively, the immobilized receptor can be mixed with the sample and the bound virus-receptor complex removed by centrifugation.

Transgenic Animal

Transgenic animals expressing the HAV receptor of the present invention are also provided. Specifically, a non-human transgenic animal expressing a nucleic acid encoding a HAV receptor having the polypeptide sequence set forth as SEQ ID NO: 1, but not expressing an endogenous active hepatitis A virus receptor is provided. In this embodiment, the foreign nucleic acid expressed in the animal is a sequence comprising the sequence set forth in the Sequence Listing as SEQ ID NO: 1. Another embodiment of the present invention is a transgenic animal expressing the sequence encoding the hepatitis A virus receptor encoded by a nucleic acid that hybridizes with the sequence set forth in the Sequence Listing as SEQ ID NO: 1 under stringency conditions described herein.

The present invention also provides transgenic animals expressing a nucleic acid encoding a regulatory domain or a binding domain of a hepatitis A virus receptor comprising a fragment of the sequence set forth in the Sequence Listing as SEQ ID NO: 1.

Uses contemplated for these transgenic animals can be, but are not limited to, methods to screen drugs, vaccines, or other compounds or substances for their anti-hepatitis A virus binding activity, methods to screen drugs, vaccines, or other compounds or substances for their anti-hepatitis A virus infection activity, methods to screen drugs, vaccines, or other compounds or substances for their hepatitis A virus therapeutic activity, or as a model animal which can be used to produce hepatitis A virus after being previously infected with HAV.

The nucleic acid used for generating a transgenic animal of the invention includes, but is not limited to, a cDNA fragment encoding a hepatitis A virus receptor or a binding domain of a hepatitis A virus receptor or a genomic sequence encoding a hepatitis A virus receptor or a binding domain of a hepatitis A virus receptor. (Ren, R., et al., Transgenic mice expressing a human poliovirus receptor: a new model for poliomyelitis. Cell 63: 353–362 (1990)). Such a genomic sequence may contain introns as well as exons, upstream and/or downstream regulatory sequences, and other functional and/or structural regions. Nucleic acids used for generating such a transgenic animal may be circular or linear molecules, and may be introduced into the animal with or without additional nucleic acids. Such additional nucleic acids include, but are not limited to, plasmid, phage, cosmid, viral, or mammalian cloning vectors, and the like. The nucleic acid may be introduced into a zygote or fertilized egg of a female animal containing two pronuclei, or embryonic stem cells prior to introducing the nucleic acid into an embryo, zygote, or fertilized egg of a female animal containing two pronuclei. The nucleic acid may be introduced into embryonic stem cells by transfection, retroviral infection, electroporation, injection, microinjection, and the like. After introduction of the foreign nucleic acid into the embryo, the embryo is transferred to the oviduct of a foster, pseudopregnant mother, and upon subsequent implantation into the uterus, the embryo may develop to term. Standard technical details of methods used to generate transgenic animals are discussed in detail by Hogan, et al., in "Manipulating the Mouse Embryo: A Laboratory Manual" (Cold Spring Harbor, N.Y.: Cold Spring Harbor Laboratory (1986)).

The transgenic animal of the present invention can be a mouse or other non-human animal selected for the presentation of characteristics sought to be altered and studied by infection with hepatitis A virus, or for practical reasons, such as ease of maintenance.

The transgenic animal of the invention can be used in a method of testing the efficacy of a hepatitis A vaccine of the invention. This method comprises administering the potential vaccine to a transgenic animal which expresses the introduced nucleic acid encoding a hepatitis A virus receptor or a binding domain of a hepatitis A virus receptor and determining whether the transgenic animal is protected from infection from hepatitis A virus. Protection of the transgenic animal from infection by hepatitis A virus may be determined in a number of ways, including, but not limited to, detecting the presence of virus in the serum, spinal fluid, plasma, blood, mucus, gastric fluids, feces, urine, and other fluids, brain tissue, liver tissue, kidney tissue, heart tissue, lung tissue, placenta tissue, skin tissue, muscle tissue, pancreatic tissue, and other tissues. Detection of virus is contemplated to distinguish between detection of virus inoculum introduced into the animal and detection of replicating virus produced as a result of a failure of a potential vaccine to prevent infection. Methods of detection for the presence of replicating virus include, but are not limited to, PCR, ELISA, IFA, Southern blotting, Western blotting, Northern blotting, plaque assay, immunocytochemical techniques, and the like.

A transgenic animal of the invention can be used in a method of producing hepatitis A virus, comprising generating a transgenic animal expressing a foreign nucleic acid encoding a hepatitis A virus receptor or a binding domain of a hepatitis A virus receptor followed by productive infection of the animal with introduced hepatitis A virus. Hepatitis A virus replicated by cells that express the introduced foreign nucleic acid (HAV receptor activity) and become infected with hepatitis A virus can be harvested by any of a number of methods known to a skilled practitioner in the art. Harvesting the replicating hepatitis A virus from a transgenic animal expressing a hepatitis A virus receptor or a binding domain of a hepatitis A virus receptor may therefore provide a source of newly synthesized hepatitis A virus for other clinical (e.g., diagnostic) or research procedures, or for vaccines.

Vectors and Hosts

Vectors comprising the nucleic acids of the present invention is also provided. The vectors of the invention can be in a host capable of expressing the polypeptide fragments contemplated by the present invention. The present invention provides a vector comprising the nucleic acid set forth in the Sequence Listing as SEQ ID NO: 1. Additionally, the present invention provides a vector comprising a nucleic acid complementary to or capable of selectively hybridizing with the nucleic acid comprising the nucleotide sequences set forth in the Sequence Listing as SEQ ID NO: 1. An alternative coding sequence for the present receptor can also be expressed.

There are numerous *E. coli* expression vectors known to one of ordinary skill in the art useful for the expression of the antigen. Other microbial hosts suitable for use include bacilli, such as *Bacillus subtilis*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carded out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosolation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or methotrexate resistance, or other genes or phenotypes suitable for use as selectable markers. The active polypeptide or polypeptide fragment coding sequence can be introduced into a Chinese hamster ovary cell line using a methotrexate resistance-encoding vector, or other cell lines using suitable selection markers. Presence of the vector RNA in transformed cells can be confirmed by Northern blot analysis and production of a cDNA or opposite strand RNA corresponding to the antigen coding sequence can be confirmed by Southern and Northern blot analysis, respectively. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from inunmoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate mediated transfection or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS-7).

The nucleic acid sequences can be expressed in hosts after the sequences have been operably linked to, i.e., positioned, to ensure the functioning of an expression control sequence. A suitable host would not express an endogenous hepatitis A virus receptor. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified antibody that specifically binds the receptor or receptor fragments of the present invention, or homologs thereof is also provided. The antibodies can be polyclonal or monoclonal. The antibodies can specifically bind a unique epitope of the receptor. "Specifically bind" as used herein describes an antibody or other ligand that does not cross react substantially with any antigen other than the one specified, in this case, the HAV receptor of the present invention. Antibodies can be made by many well-known methods (see also, Harlow and Lane, Antibodies; A Laboratory Manual, Cold Spring Harbor Laboratory, Cold Spring Harbor, N.Y., (1988)). Briefly, purified virus or viral antigen can be injected into an animal in an mount and in intervals sufficient to elicit an immune response. Antibodies can either be purified directly, or spleen cells can be obtained from the animal. The cells are then fused with an immortal cell line and screened for antibody secretion. The antibodies can be used to screen nucleic acid clone libraries for cells secreting the antigen. Those positive clones can then be sequenced as described in the Examples or by other methods (see, for example, Kelly et al., Bio/Technology, 10: 163–167 (1992); Bebbington et al., Bio/Technology, 10: 169–175 (1992)).

The antibody can be bound to a substrate or labeled with a detectable moiety or both bound and labeled. The detectable moieties contemplated with the composition of the present invention can be those listed above in the description of the detection methods, including fluorescent, enzymatic and radioactive markers.

Vaccines

The virus receptor or viral receptor antigen, e.g., a purified antigenic polypeptide fragment encoded by the nucleic acids of this invention, can be used in the construction of a vaccine comprising an immunogenic amount of the virus receptor or antigen and a pharmaceutically acceptable carrier. The vaccine can be the entire antigen, the antigen on the intact receptor, E. coli or other strain, or an epitope specific to the antigen. The vaccine can also be potentially cross-reactive with antibodies to other antigens. The vaccine can then be used in a method of preventing infection with the HAV described herein.

The purified polypeptide or fragments of the HAV receptor can be tested to determine their immunogenicity and specificity for use as a vaccine. Briefly, various concentrations of a putative immunogen are prepared and administered to an animal and the immunological response (e.g., the production of antibodies or cell mediated immunity) of an animal to each concentration is determined. Thereafter an animal so inoculated with the immunogen can be exposed to the virus to test the potential vaccine effect of the specific immunogenic fragment. The specificity of a putative immunogenic fragment can be ascertained by testing sera, other fluids or lymphocytes from the inoculated animal for cross reactivity with other closely related picornaviruses.

Immunogenic amounts of the vaccine antigen can be determined using standard procedures. Briefly, various concentrations of a putative specific immunoreactive epitope are prepared, administered to a subject and the immunological response (e.g., the production of antibodies or cell mediated immunity) of the subject to each concentration is determined. The amounts of antigen administered depend on the subject, e.g. a human or a guinea pig, the condition of the subject, the size of the subject, etc.

Accordingly, therefore, the present invention provides a vaccine comprising the HAV receptor, an immunogenic polypeptide or fragments of the polypeptide. Examples of such polypeptides include those derived from a purified polypeptide encoded by the nucleotide sequences set forth in the Sequence Listing as SEQ ID NO: 1. Such a vaccine would naturally include immunogenic amounts of the virus receptor or polypeptide fragments and a pharmaceutically acceptable carrier.

The pharmaceutically acceptable carrier contemplated herein can comprise saline or other suitable carriers (Arnon, R. (Ed.) Synthetic Vaccines I: 83–92, CRC Press, Inc., Boca Raton, Fla., (1987)). By "pharmaceutically acceptable" is meant a material that is not biologically or otherwise undesirable, i.e., the material may be administered to an individual along with a selected compound without causing any undesirable biological effects or interacting in a deleterious manner with any of the other components of the pharmaceutical composition in which it is contained. The carrier will depend upon the method of administration and choice of adjuvant if one is used. An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention contemplates methods of preventing or treating infection from hepatitis A virus and the associated diseases by administering the vaccine to a subject.

Although the present process has been described with reference to specific details of certain embodiments thereof, it is not intended that such details should be regarded as limitations upon the scope of the invention recited in the accompanying claims.

EXAMPLE

Isolation of DNA Encoding the HAV Receptor

Cloning

The nucleic acid encoding the hepatitis A virus (HAV) receptor (SEQ ID NO: 1) was isolated by cloning the cDNA population of a primary African Green Monkey Kidney (AGMK) cell line expressing the HAV receptor (BioWhittaker, Inc. Walkersville, Md., USA, cell line #70-161A). (Murphy, A. J. M., et al., cDNA expression cloning in human cells using the pλDR2 episomal vector system. Meth. in Enzymology 4: 111–131 (1992)). Other commercially available monkey-derived primary kidney cell lines can be substituted for the cell line used here. The cDNA was cloned into the mammalian expression vector pDR2 containing the Rous Sarcoma Virus LTR promoter, a pBR322 bacterial origin of replication, an Epstein-Barr Virus origin of replication which confers stable episomal maintenance, a hygromycin gene for growth and selection in eukaryotic cells, and the ampicillin resistance gene for growth and selection in bacteria (Clontech Laboratories, Inc., Palo Alto, Calif., USA) using the method of Murphy, A. J. M., et al.

Transfection of HeLa Cells to Generate E14C Cells

The cloned cDNA's were then transfected into EBNA-1-expressing human HeLa cells to generate the E 14C cell line (as described but not specifically designated "E14C" by Murphy, ,A. J. M., et al.) which does not normally express a HAV receptor.

Selection of Transfected Cells

Transfected, hygromycin resistant cells expressing the cloned HAV receptor were selected using a monoclonal antibody designated 190-4 in an antibody panning protocol. (Arruf and Beed, Proc. Nat. Acad. Sci. 84: 8573–8577 (1987)).

Transformation of *E. coli*

Episomal DNA was extracted from the cells bound to the antibody and transformed into *Escherichia coli* (*E. coli*). (Murphy, A. J. M., et al.)

Identification of Plasmids Coding for the Hepatitis A Virus Receptor

Transformed, ampicillin resistant *E. coli* cells were selected and the plasmid DNA from these cells purified and used to again transfect human E14C cells, which do not express the HAV receptor, by the methods described above. Expression of the HAV receptor was determined using an antibody to the receptor by the methods described by Murphy, .J. M, et al. A plasmid coding for this epitope was designated pDR2-HAVcr5 (submitted to ATCC on Aug. 3, 1994). Plasmid pDR2-HAVcr5 was transfected into guinea pig GPC-16 (ATCC No. CCL 242) and mouse Ltk$^-$ cells (ATCC No. 1.3).

These cells were then exposed to HAV to determine whether they had become permissive for HAV infection. Control GPC-16 and Ltk$^-$ cells transfected with the shuttle vector alone were also exposed to HAV to serve as a control. After two to five weeks, cells that became infected were detected by indirect immunofiuorescence using HAV-neutralizing murine monoclonal antibodies K2-4F2, K3-4C8, and K3-2F2(Commonwealth Serum Laboratories, Parkville, Victoria, Australia). (MacGregor, ,A., et al., J. Clin. Microbiol. 18: 1237–1243 (1983)). Other methods such as slot blot, dot blot, or Northern blot hybridization, using a probe to the HAV cDNA can also be use to detect infection. Cells transfected with cDNA encoding the biological activity of a hepatitis A virus receptor became infected with HAV, whereas cells transfected with the shuttle vector alone were not permissive for HAV infection.

The cDNA isolated from the cells transformed into HAV permissive cells was isolated and sequenced using the dideoxynuclotide sequencing technique. (Sanger, F., et al. DNA sequencing with chain-terminating inhibitors. Proc. Nat. Acad. Sci. 74: 5463 (1977)). The sequence obtained was checked for its originality against the GENBANK database and no sequences with greater than 55% identity to the present invention were found.

Detection of HAV Receptor Coding Sequence in Other Cells

Isolated DNA from the monkey cells lines GL-37 (another primary AGMK cell line), CV-1 (ATCC No. CCL 70), BSC-1 (ATCC No. CCL 26), and FRhK-4 (ATCC No. CRL 1688), and from human cell lines HeLa (ATCC No. CCL 2) and MRC-5 (ATCC No. CCL 171) were tested for the presence of a HAV receptor gene by Southern blot analysis using the entire sequence set forth in the Sequence Listing as SEQ ID NO: 1 as the probe under hybridization stringency conditions of 45° C., 50% formamide and 5X SSC followed by washing stringency conditions of 65° C. and 0.2X SSC with 0.1% SDS. All of these cell lines tested positive for a DNA fragment which hybridized to the probe under the stated stringency conditions. DNA isolated from the Ltk$^-$ and GCP-16 cell lines used for the second round of transfection were also analyzed under identical conditions but did not test positive for hybridization to the probe. DNA can be isolated from cells and cloned using a selectively hybridizing nucleic acid as described above in order to isolate, sequence and express the DNA encoding HAV receptors from other animals as exemplified by the sequence described above.

Detection of Messenger RNA Encoding the HAV Receptor from other Cells

Poly A$^+$RNA was isolated from the monkey cell line GL-37, mouse Ltk$^-$ cells, human HeLa cells, chimpanzee liver tissue, and from human heart, brain, placenta, lung, liver, skeletal muscle, kidney, and pancreas tissue. Poly A$^+$RNAs from these samples were electrophoresed on formaldehyde gels and probed by Northern blot hybridization for the presence of message corresponding to a hepatitis A virus receptor. Two stringency conditions for these Northern blot were used: (1) a hybridization stringency condition of 42° C., 50% formanide and 50% formamide, followed by a washing stringency condition of 65° C., 2X SSC and 0.1% SDS using the sequence set forth in the Sequence Listing as SEQ ID NO: 3 as a probe (corresponding to nucleotides 123 through 425 of the sequence set forth in the Sequence Listing as SEQ ID NO: 1); or (2) a hybridization stringency condition of 42° C. and 5X SSPE, followed by the washing stringency condition of 42° C., 2X SSC and 0.1% SDS (sodium dodecyl sulfate) using the sequences set forth in the Sequence Listing as SEQ ID NO: 4 and SEQ ID NO: 5 as probes (corresponding to nucleotides 251 through 330 and 1467 through 1547 of the sequence set forth in the Sequence Listing as SEQ ID NO: 1, respectively).

The results of these Northern blots show that poly A$^+$RNA hybridizing to the probes derived from the sequence of the cloned hepatitis A virus receptor of the present invention was detected in all tissues and poly A$^+$RNAs tested except the RNA from the mouse cell line. Tissues permissive for HAV, therefore, appear to express a gene which hybridizes to the HAV receptor probes. The banding pattern of the Northern blot indicates that a gene which hybridizes to the probes derived from the sequence of the cloned hepatitis A virus receptor was more prevalent in poly A$^+$RNA isolated from the human liver than from the other tissues or cell lines (see, FIG. 1). This indicates that a homologous gene is expressed to high levels in the human liver. This gene can be cloned, sequenced, and expressed, according to the methods used herein, among others known in the art.

In this manner the human homolog of the hepatitis A virus receptor of SEQ ID NO: 1 was identified in human liver tissue by selective hybridization under the above stringency conditions.

Comparison to Unrelated Hepatitis A Virus Binding Protein

In order to determine that the present hepatitis A virus receptor is distinct from the HAV binding protein disclosed by Anderson, D. A., et al., a binding assay similar to the experiment performed by Anderson, et al. was performed using the polypeptide set forth in the Sequence Listing as SEQ ID NO: 1. The protein disclosed by Anderson, et al binds to hepatitis A virus after the protein has been immobilized on nitrocellulose membranes. The present purified hepatitis receptor does not bind virus after immobilization and is therefore different and distinguishable from the protein disclosed by Anderson, et al.

Additionally, binding experiments using the protein disclosed by Anderson, et al. were performed. These experiments showed that the protein disclosed by Anderson, et al. binds nonspecifically to RNA (e.g. Anderson, et al.'s RNA probe) and does not bind the hepatitis A virus itself. The protein isolated by Anderson, et al., is therefore not a hepatitis A virus receptor, but rather an RNA binding protein. In contrast, the data regarding the present receptor specifically shows that transfection of previously nonpermissive cells with an expression vector containing a cDNA encoding the isolated receptor transforms these cells into hepatitis A virus infection permissive cells.

What is claimed is:

1. An isolated nucleic acid comprising a nucleic acid encoding a hepatitis A virus receptor consisting of the polypeptide set forth in the Sequence Listing as SEQ ID NO: 2.

2. The isolated nucleic acid of claim 1 in a vector suitable for expressing the nucleic acid.

3. The vector of claim 2 in a host suitable for expressing the nucleic acid.

4. The isolated nucleic acid of claim 1, wherein the nucleic acid comprises the nucleic acid set forth in the Sequence Listing as SEQ ID NO: 1.

5. An isolated nucleic acid encoding a hepatitis A virus receptor having a native amino acid sequence, which hybridizes with the nucleic acid set forth in the Sequence Listing as SEQ ID NO: 1 under the stringency conditions of 42° C. and 5X SSPE, followed by the washing conditions of 42° C., 2X SSC and 0.1% sodium dodecyl sulfate.

6. The isolated nucleic acid of claim 5 in a vector suitable for expressing the nucleic acid.

7. The vector of claim 6 in a host suitable for expressing the nucleic acid.

8. An isolated cell line which expresses a non-endogenous nucleic acid of claim 5.

* * * * *